Nov. 26, 1963 J. M. GARABEDIAN Plant Pat. 2,323

NECTARINE TREE

Filed Oct. 29, 1962

WITNESS

Addison E. Avery

INVENTOR

John M. Garabedian

Webster & Webster
ATTYS.

United States Patent Office

Plant Pat. 2,323
Patented Nov. 26, 1963

2,323
NECTARINE TREE

John M. Garabedian, Fresno, Calif., assignor to Peach & Willow Farms, Inc., Fresno, Calif., a corporation of California Filed Oct. 29, 1962, Ser. No. 233,989
1 Claim. (Cl. Plt.—41)

This invention relates to a new and distinct variety of nectarine tree; the variety having been originated by me, in an experimental orchard located near Fresno, California, as a seedling of an unnamed and unpatented mutation of the Sun Grand nectarine (United States Plant Patent No. 974).

When such seedling came into bearing—and upon recognition by me of its distinctive characteristics, which will hereinafter appear—I accomplished asexual reproduction of the variety by budding onto mature nectarine trees in the aforesaid experimental orchard. Such asexual reproductions ran true to the parent in all respects.

The present variety, while having general resemblance to the Sun Grand in tree and fruit, is—in comparison—substantially distinct by reason of:

Flowers which have light yellow anthers similar to the unpatented J. H. Hale peach, and which is indicative of pollen sterility.

Fruit which is in harvest approximately four weeks earlier than the Sun Grand; is semi-freestone instead of fully free; is similar in shape but has a brighter red exterior or skin color and less red in the flesh; and is of a better eating quality, being less acid.

Figures 1, 2:
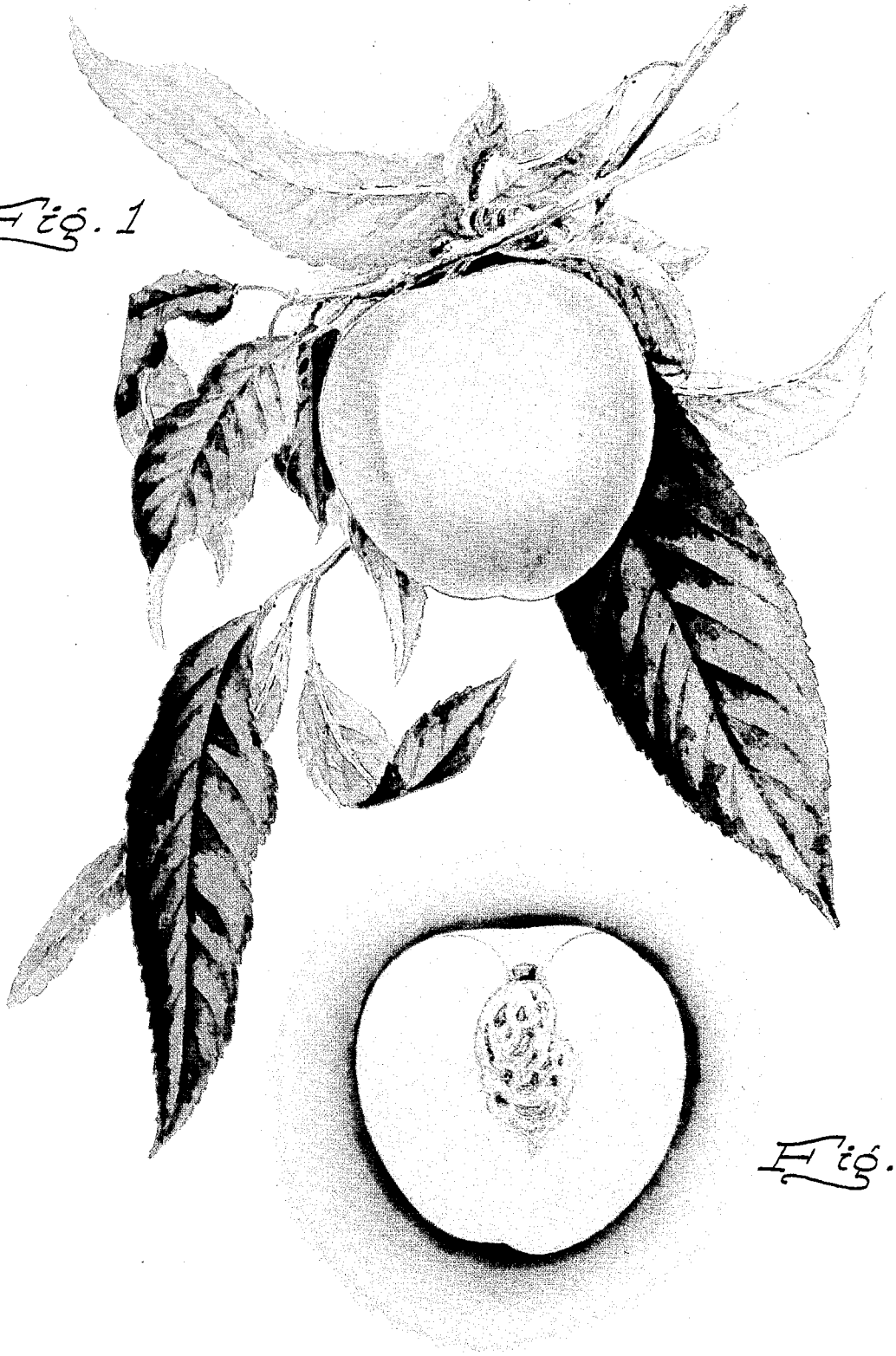
FIG. 1 is an elevation showing one of the fruit, together with twigs and leaves.
FIG. 2 is a sectional elevation of one of the fruit, with the stone remaining in place.

Referring now more specifically to the pomological details of this new and distinct variety of nectarine tree, the following is an outline description thereof; all major color plate identifications being by reference to Maerz and Paul Dictionary of Color except where common terms of color definition are employed.

Tree:
- *Size.*—Large.
- *Vigor.*—Vigorous.
- *Growth.*—Spreading.
- *Density.*—Dense.
- *Hardiness.*—Hardy.
- *Production.*—Productive.

Trunk:
- *Size.*—Stocky—medium.
- *Texture.*—Medium.

Branches:
- *Size.*—Medium.
- *Texture.*—Medium.
- *Color.*—Brown.
- *Lenticels.*—Number—medium.

Leaves:
- *Size.*—Medium. Average length—4" to 6½". Average width—1¼" to 1⅝".
- *Form.*—Lanceolate; acutely pointed.
- *Thickness.*—Medium.
- *Surface.*—Smooth—some leaves slightly rugose.
- *Color.*—Top side—medium green (23–L–6). Under side—lighter green (21–L–7).
- *Margin.*—Crenate.
- *Petiole.*—Medium length; medium thickness.
- *Glands.*—Average number—three to four. Irregular; medium to small; globose; usually positioned two on petiole and one to two on margin at base of leaf.

- *Stipules.*—Present but early dehiscent.

Flower buds: Hardy.

Flowers:
- *Blooming period.*—Date of first bloom—March 1st. Date of full bloom—March 10th. Medium as compared with other varieties.
- *Size.*—Large.
- *Color.*—Pink.
- *Pollen.*—Sterile.

Fruit:
- *Maturity when described.*—Hard ripe—June 1st–June 5th.
- *Date of first picking.*—June 1st.
- *Date of last picking.*—June 5th.
- *Comparative harvest.*—Approximately four weeks earlier than Sun Grand.
- *Size.*—Uniform; medium.
- *Form.*—Uniform; globose; slightly compressed transversely toward suture; slightly compressed on ventral side toward apex.
- *Suture.*—Shallow; extends from base to beyond apex; slight depression beyond pistil point.
- *Ventral surface.*—Rounded strongly; lips equal.
- *Cavity.*—Rounded; slightly elongated in suture plane, with suture showing on one side. Average depth—½". Average breadth—⅝".
- *Base.*—Rounded.
- *Apex.*—Short; rounded.
- *Pistil point.*—Apical.

Skin:
- *Thickness.*—Medium.
- *Texture.*—Medium.
- *Tendency to crack.*—None in dry season.
- *Down.*—Wanting.
- *Color.*—Orange red to red (shading from 3–A–12 to 3–K–11 to 3–J–12).

Flesh:
- *Amygdalin.*—Scant.
- *Texture.*—Firm.
- *Fibers.*—Few; fine.
- *Ripens.*—Evenly.
- *Flavor.*—Slightly acid but good balance with sugar.
- *Aroma.*—Distinct.
- *Eating quality.*—Good.
- *Color.*—Yellow (10–K–5 shading to 10–A–9), with red (3–K–5) at stone.

Stone:
- *Type.*—Semi-free; adheres to flesh along both dorsal and ventral edges; adheres slightly to flesh toward base of stone when fully ripe; free on sides; fibers short.
- *Size.*—Medium. Average length—1 5/16". Average breadth—1". Average thickness—¾".
- *Form.*—Oblong.
- *Base.*—Straight.
- *Apex.*—Acute.
- *Sides.*—Equal.
- *Surface.*—Irregularly furrowed near base; irregularly pitted throughout.
- *Ridges.*—Rounded; jagged toward base.
- *Pits.*—Elongated.
- *Dorsal edge.*—Full with shallow groove.
- *Tendency to split.*—Slight.
- *Color.*—Tan (3–A–10), with darker pitting (6–F–9).

Use: Market; shipping.

Keeping quality: Good.

Shipping quality: Good.

The tree and its fruit herein described may vary in slight detail due to climatic and soil conditions under which the variety may be grown; the present description being of the variety as grown near Fresno, California.

The following is claimed:

A new and distinct variety of nectarine tree, as illustrated and described, which bears general resemblance to the Sun Grand in tree and fruit, but—in comparison—is substantially distinct by flowers having light yellow anthers and sterile pollen, and by fruit which is in harvest approximately four weeks earlier, is semi-freestone instead of fully free, is of a brighter red exterior color with lesser red in the flesh, and is of better eating quality, being less acid.

No references cited.